United States Patent [19]

Norris

[11] Patent Number: 5,283,355
[45] Date of Patent: Feb. 1, 1994

[54] BENZOQUINONE COMPOUNDS

[75] Inventor: William J. E. Norris, New Mill, England

[73] Assignee: Imperial Chemical Industries PLC, London, England

[21] Appl. No.: 780,470

[22] Filed: Oct. 22, 1991

[30] Foreign Application Priority Data

Oct. 25, 1990 [GB] United Kingdom ............... 9023290.1
Oct. 25, 1990 [GB] United Kingdom ............... 9023291.9

[51] Int. Cl.$^5$ .................... C07C 50/02; C07C 225/28; C07D 205/02; C07D 237/02
[52] U.S. Cl. .................................. 552/306; 552/307; 540/200; 540/202; 548/240; 548/250; 548/300.1; 548/356.1; 548/400; 546/1; 546/84; 546/100; 546/122; 546/123; 546/124; 546/125; 546/146; 546/215; 549/1; 549/13; 549/14; 549/20; 549/30; 549/83; 549/88; 549/89; 549/356; 549/357; 549/429; 549/430; 549/510; 544/1; 544/2; 544/3; 544/7; 544/53; 544/63; 544/66; 544/88; 544/98; 544/179; 544/180; 544/224; 544/242; 544/336
[58] Field of Search ................ 552/306, 307; 540/200, 540/202; 544/1, 2, 3, 63, 179, 180, 224, 7, 53, 66, 88, 98, 242, 336; 546/84, 100, 122, 123, 124, 125, 146, 215; 548/240, 250, 300.1, 356.1, 400; 549/1, 13, 14, 20, 30, 83, 88, 89, 356, 357, 429, 430, 510

[56] References Cited

U.S. PATENT DOCUMENTS 2,229,099  1/1941  Langbein ............................ 552/307
2,267,741 12/1941  Langbein ............................ 552/307
2,288,198  6/1942  Langbein ............................ 552/307
4,519,948  5/1985  Hsu et al. ........................... 552/307

OTHER PUBLICATIONS

Chemical Abstract, vol. 91, 1979, Abstract No. 175149M, p. 645.

Primary Examiner—Howard T. Mars
Assistant Examiner—Kimberly J. Kestler
Attorney, Agent, or Firm—Cushman, Darby & Cushman

[57] ABSTRACT

Compounds of the Formula (5) and processes for their preparation and use, particularly in the manufacture of unsymmetrical triphenodioxazine dyes:

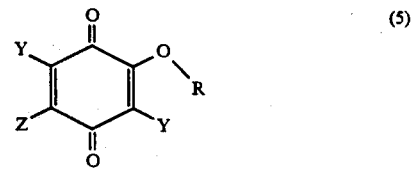

(5)

wherein:
Y is H, alkyl, substituted alkyl, alkoxy, Cl or Br;
R is a group of Formula (3)

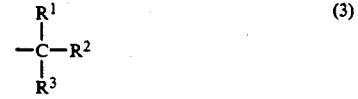

(3)

$R^1$ and $R^2$ are each independently alkyl, or $R^1$ and $R^2$ together with the carbon atom to which they are attached form an optionally substituted 4, 5 or 6 membered alicyclic or heterocyclic ring;
$R^3$ is H;
Z is Cl, Br or A—NH; and
A is H or the residue of a primary amine.

6 Claims, No Drawings

BENZOQUINONE COMPOUNDS

This specification describes an invention related to benzoquinone compounds and processes for their manufacture and use. The benzoquinone compounds are of particular value in the manufacture of triphenodioxazine (TPD) derivatives and in particular unsymmetrical TPD derivatives which can be used as dyestuff chromophores.

Mono-ethers formed from the reaction of a primary alcohol and a tetrachlorobenzoquinone (TCBQ) are useful as intermediates for the preparation of dyestuffs. For example methanol reacts with TCBQ in the presence of alkali to give a mixture of products containing the mono-ether 2-methoxy-3,5,6-trichloro-1,4-benzoquinone (MTBQ) together with significant quantities of the bis-ether 2,5-dimethoxy-3,6-dichloro-1,4-benzoquinone.

In circumstances where the mono-ether is desired the formation of bis-ether is undesirable since it is both wasteful of TCBQ and gives rise to purification difficulties. It is therefore desirable to increase the ratio of mono:bis ether formed as much as possible in order to optimise the efficiency and reduce the cost of manufacturing mono-ether derivatives of TCBQ.

We have now discovered that a mono-ether formed from reaction of a halogenobenzoquinone with a secondary alcohol is a valuable intermediate in the preparation of triphenodioxazine (TPD) chromophores, particularly unsymmetrical TPD chromophores. Furthermore, the reaction of a secondary alcohol with a halogenobenzoquinone gives a higher ratio of mono:bis ether than when a primary alcohol is used, and this is of great value where mono-ether is desired.

According to the first aspect of the present invention there is provided a process for the preparation of a compound of the Formula (1)

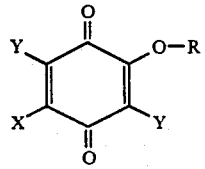
(1)

comprising condensing a compound of Formula (2) with a hydroxy compound of formula R—OH;

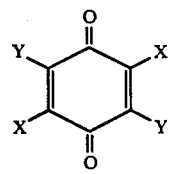
(2)

wherein:
Y is H, alkyl, substituted alkyl, alkoxy, Cl or Br;
R is a group of Formula (3)

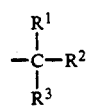
(3)

$R^1$ and $R^2$ are each independently alkyl, or $R^1$ and $R^2$ together with the carbon atom to which they are attached form an optionally substituted 4, 5 or 6 membered alicyclic or heterocyclic ring;
$R^3$ is H; and
X is Cl or Br.

Y is preferably H, $C_{1-4}$-alkyl, substituted $C_{1-4}$-alkyl, $C_{1-4}$-alkoxy, Cl or Br. It is more preferred that Y is Cl, Br or $C_{1-4}$-alkyl, especially methyl or tertiary butyl.

It is preferred that R is derived from a compound of formula R-OH which is capable of being removed by distillation after the compound of Formula (1) has been prepared. It is more preferred that R is derived from a compound of formula R—OH with a boiling point of below 200° C., more preferably below 170° C., especially in the range 50°–150° C.

It is preferred that $R^1$ and $R^2$ are each independently $C_{1-4}$-alkyl, substituted $C_{1-4}$-alkyl or $R^1$ and $R^2$, together with the carbon atom to which they are attached, form an optionally substituted 5 or 6 membered heterocyclic or preferably alicyclic ring. It is especially preferred that $R^1$ and $R^2$ are each independently $C_{1-4}$-alkyl or that $R^1$ and $R^2$ together with the carbon atom to which they are attached form a cyclohexyl or cyclopentyl group.

X is preferably Cl.

It is particularly preferred that X and Y are chloro.

As examples of the group —OR in Formula (1) there may be mentioned secondary aralkoxy groups such as sec-phenethyloxy, more preferably cyclopentyloxy or cyclohexyloxy, and especially iso-propoxy because iso-propanol (from which —OR may be derived) is cheap and sufficiently volatile to be removed from a compound of Formula (1), if desired, by distillation at convenient temperatures.

The compounds of Formula (1) are particularly useful as intermediates for the manufacture of triphenodioxazine dyes, especially unsymmetrical triphenodioxazine dyes.

It is preferred that the above process is performed at essentially constant pH by metered addition of alkali during the process. The identity of the alkali used in the above process is not believed to be critical; however the preferred alkali comprises an alkali metal hydroxide, carbonate, bicarbonate or acetate alkali metal hydroxide, carbonate, bicarbonate or acetate or mixture thereof, especially sodium hydroxide, sodium acetate, sodium carbonate, sodium bicarbonate, lithium hydroxide, potassium hydroxide and potassium acetate.

It is preferred that the process is performed above 30° C., more preferably above 40° C., especially at a temperature from 40° C. to 100° C. It is also preferred that the reaction is performed in a solvent, which is optionally a hydroxy compound of formula R—OH.

Examples of further solvents in which the above process can be carried out include conventional aprotic solvents; for example, chlorinated hydrocarbons such as $CCl_4$, $CHCl_3$ and $CH_2Cl_2$; ethers such as diethyl ether, di-isopropyl ether, di-phenyl ether; aromatic solvents such as xylene and toluene; but preferably ketone solvents such as acetone, methyl ethyl ketone or methyl isobutyl ketone are used.

We have also found that when MTBQ is reacted with a primary amine a mixture results which contains a mono-amine adduct in which the 5-chloro group is displaced by the amine, and a bis-amine adduct in which both the 5-chloro and 2-methoxy groups have been displaced by the same amine. In the manufacture of unsymmetrical TPD dyes, such as those described in EP 0432879, it is desirable to increase the ratio of mono-to bis-amine adduct as far as possible so that the monoadduct can be reacted with a second amine (which is different to the first amine) under more forcing conditions to give a desired unsymmetrical bis-amine adduct, such as a dianilide, which may in turn be cyclised to give an unsymmetrical TPD dyebase.

We have now found that a compound of Formula (1) may be reacted with a primary amine to give a particularly high ratio of mono-to bis- adduct.

According to the second aspect of the present invention there is provided a process for the preparation of a compound of the Formula (4) which comprises condensing ammonia or an amine of formula A—NH$_2$ with a compound of Formula (1):

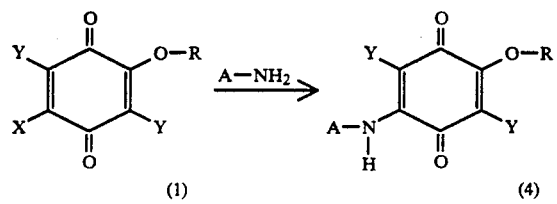

wherein R, X, and Y are as hereinbefore defined and A is H or the residue of a primary amine.

It is preferred that the process according to the second aspect of the invention is performed using 0.8 to 1.2, more preferably 0.9 to 1.1, especially about 1 molecular equivalent of ammonia or amine of formula A—NH$_2$ per 1 molecular equivalent of compound of Formula (1).

A preferred process for the preparation of the compounds of Formula (4) comprises the process according to the first aspect of the present invention followed by the process of the second aspect of the present invention.

A is preferably H; optionally substituted alkyl, especially C$_{1-4}$-alkyl; or optionally substituted aralkyl, especially phenyl-C$_{1-4}$-alkyl; but is more preferably optionally substituted aryl, especially optionally substituted phenyl. When A is substituted it preferably has 1 or 2 substituents which are the same as each other or are different.

When A is optionally substituted phenyl it has been found that symmetrical dianilide impurities (i.e. where one mole of the compound of Formula (1) has reacted with 2 moles of the amine A—NH$_2$) can conveniently be removed by filtration; the desired product of Formula (4) remaining in solution whilst less soluble symmetrical dianilinide may be filtered off.

The optional substituents present on A are preferably of the formula —(X—B)$_a$—W wherein:

X is O, S, SO, SO$_2$, N(R$^4$) wherein R$^4$ is H or an optionally substituted hydrocarbon radical;
B is an optionally substituted divalent hydrocarbon radical;
a is 0, 1 or 2;
W is O(C$_{1-4}$-alkyl), OC$_n$H$_{2n}$OH, OC$_n$H$_{2n}$O(C$_{1-4}$-alkyl), OC$_n$H$_{2n}$NR$^5$R$^6$, SH, S(C$_{1-4}$-alkyl), —SC$_n$H$_{2n}$OH, SC$_n$H$_{2n}$NR$^5$R$^6$, NR$^5$R$^6$, NR$^5$C$_n$H$_{2n}$OH, NR$^5$C$_n$H$_{2n}$NR$^5$R$^6$, C$_{1-4}$-alkyl, SO$_3$H, CO$_2$H, or halo; each n has a value of 2, 3 or 4; and
R$^5$ and R$^6$ are each independently H or an optionally substituted hydrocarbon radical.
X is preferably O, S or N(R$^4$).

When any of the groups R$^1$ to R$^6$, R or B is substituted it is preferred that the substituent or substituents are selected from halo, especially chloro; —CO$_2$H;

—SO$_3$H; —NH$_2$; —CN; C$_{1-4}$-alkoxy, especially methoxy; C$_{1-4}$-alkyl, especially methyl; and acetamido.

Optionally substituted divalent hydrocarbon radicals represented by B are preferably optionally substituted alkylene, aralkylene and arylene radicals and the preferred optional substituents are selected from sulpho, hydroxy and C$_{1-4}$-alkyl. When B is alkylene it preferably has less than seven carbon atoms, more preferably from two to four carbon atoms. When B is aralkylene it preferably contains from seven to fourteen carbon atoms such as C$_{1-4}$-alkylenephenyl or C$_{1-4}$-alkylenenaphthyl. When B is arylene it is preferably optionally substituted phenylene or naphthylene.

As examples of alkylene and aralkylene radicals which may be represented by B there may be mentioned:
1,2- and 1,3-propylene
2-hydroxy-1,3-propylene
1- and 2-phenyl-1,3-propylene
1,4-, 2,3- and 2,4-butylene
2-methyl-1,3-propylene
2-methyl-2,4-pentylene
2,2-dimethyl-1,3-propylene
1-phenylethylene
1-chloro-2,3-propylene
1,6- and 2,5-hexylene
2,3-diphenyl-1,4-butylene
1-(methoxycarbonyl)-1,5-pentylene
2,7-heptylene
3-methyl-1,6-hexylene —CH$_2$CH$_2$OCH$_2$CH$_2$——CH$_2$CH$_2$SCH$_2$CH$_2$——CH$_2$CH$_2$SSCH$_2$CH$_2$—

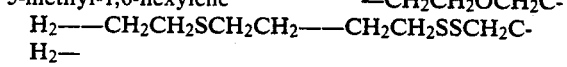

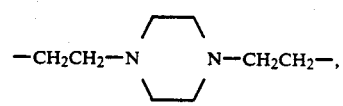

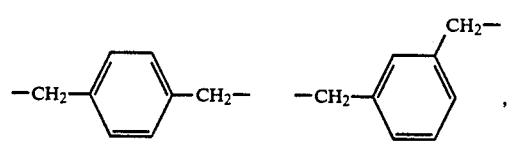

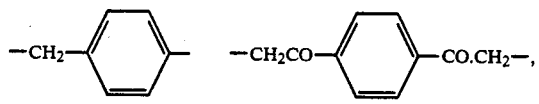

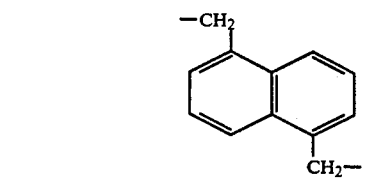

As examples of arylene radicals which may be represented by B there may be mentioned 1,2-, 1,3- and 1,4-phenylene, 1,4-naphthylene and 1,5-naphthylene which are substituted by less than four, and preferably less than three sulpho groups.

When any of R$^4$, R$^5$ and R$^6$ are optionally substituted hydrocarbon radicals they are preferably optionally substituted alkyl, cycloalkyl, aralkyl and aryl radicals, more preferably alkyl radicals, especially C$_{1-4}$-alkyl radicals which may be substituted by halogen, hydroxy or cyano, but preferably are free from substituents.

As examples of groups represented by A there may be mentioned: phenyl;
2, 3 or 4-aminophenyl;
2, 3 or 4-methylthiophenyl;
2, 3 or 4-methoxyphenyl;
2, 3 or 4-acetamidophenyl;
2, 3 or 4-trifluoracetamidophenyl;
and phenyl substituted by a group selected from:
$SO_2(CH_2)_n$- W;
$NH(CH_2)_n$- W;
$O(CH_2)_n$- W;
$S(CH_2)_n$- W;
$SO(CH_2)_n$- W;
4-aminophenylamino;
wherein W is as defined above, and is preferably OH, $NH_2$ or $OSO_3H$, and n has a value of 2 or 3.

As examples of other optionally substituted aryl groups represented by A there may be mentioned para-diphenyl, N-ethyl-carbazol-3-yl, beta-anthracinyl, alpha-naphthyl, beta-anthraquinonyl, 6-hydroxy-7-carboxynaphth-2-yl and 4-hydroxy-3-carboxyphenyl.

The compounds of Formula (4) are particularly useful as intermediates for the manufacture of unsymmetrical dianilinides used in the manufacture of unsymmetrical TPD dyes, such as those described in EP 0432879.

The process according to the second aspect of the invention in which R is of Formula (3) results in a particularly high ratio of mono:bis amine adduct compared with that when R is methyl. The product of the process can, if required, be further purified to remove any residual quantities of bis-amine adduct using known technology, such as preparative high pressure chromatography, crystallisation or distillation as appropriate, or, depending on the relative solubilities of mono- to bis-amine adduct, they may be separated simply by filtering off the least soluble adduct. However, the ratio of mono:bis-amine adduct is normally sufficiently high to make such further purification unnecessary and commercially undesirable.

It is preferred that the process of the second aspect of the present invention is performed above 30° C., more preferably above 40° C., preferably below 110° C. and especially from 40° to 100° C. It is also preferred that the reaction is performed in a solvent, and at a pH of approximately 4 to 9, especially 5.0 to 5.8.

It is preferred that the process of the second aspect of the invention is maintained in the aforementioned pH range by the addition of alkali during the process, the identity of which is not believed to be critical; however the above mentioned alkali are preferred, especially aqueous NaOH or KOH. It is preferred that the pH is maintained essentially constant during the process of the second aspect of the invention.

Examples of solvents in which the process according to the second aspect of the invention can be carried out include those aprotic solvents mentioned in respect of the first aspect of the invention and protic solvents such as $C_{1-4}$-alkanols, especially propan-2-ol and propan-1-ol.

According to a third aspect of the invention there is provided a compound of the Formula (5):

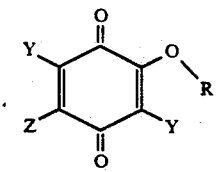

wherein R and Y are as hereinbefore defined and Z is Cl, Br or A—NH— wherein A is as hereinbefore defined.

The present invention is intended to relate not only to mono-amine adducts of Formula (5) (in which Z is A—NH-) but also to mixtures containing a ratio of such mono-amine adduct to bis-amine adduct (wherein —O—R is also of formula —NH—A) in the ratio of at least 60:40, preferably at least 70:30, and up to 95:5, and especially from 75:25 to 90:10.

According to a fourth aspect of the present invention there is provided a process for the manufacture of a compound of Formula (6) which comprises condensing a compound of Formula (4) (as defined above) with an amine of formula $A^1$—$NH_2$, preferably in the presence of alkali, wherein $A^1$ is as defined by A above, provided that A and $A^1$ are different.

The fourth aspect of the present invention is illustrated by the following formulae:

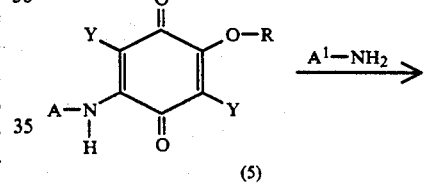

wherein A and $A^1$ are each as defined for A above and are different to each other, Y and R are as defined above.

The preferred alkali and solvents and temperature used in the fourth aspect of the invention are as described in the second aspect of the present invention, but more forcing conditions are preferred for the second amine to displace the group represented by —O—R, that is to say a higher temperature than used in the second aspect, e.g. 50°-100° C. and/or higher pH e.g. approximately pH 6 to 7. The presence of water, for example by performing the process in aqueous organic solvent or in water, also facilitates the process of the fourth aspect of the present invention. The aqueous organic solvent preferably comprises a water miscible organic solvent and at least 5%, preferably at least 10% water.

According to a fifth aspect of the present invention there is provided a process for the preparation of aminobenzoquinone compounds of Formula (6) comprising the steps of (i) condensing a compound of Formula (1) with a first amine of formula A—$NH_2$ to give a compound of Formula (4) according to the process described in the second aspect of the present invention; and (ii) condensing the product of step (i) with a compound of formula $A^1—NH_2$ to give the compound of Formula (6) according to the fourth aspect of the present invention, wherein X, Y, R, A and $A^1$ are as defined respectively in each aspect of the invention.

A preferred embodiment of the fifth aspect of the present invention includes the additional step of preparing the compound of Formula (1) according to the first aspect of the invention.

The sequential additions of the amines $A—NH_2$ and $A^1—NH_2$ (i.e. steps (i) and (ii)) described in the fifth aspect of the present invention) may optionally be performed in the same reaction vessel. The preferred temperatures, solvents and alkali for steps (i) and (ii) are as described above in the second and fourth aspects of the invention respectively.

According to a sixth aspect of the present invention there is provided a process for the preparation of an unsymmetrical TPD compound comprising the steps (i) preparing a dianilinide of Formula (6) according to the process described in the fourth aspect of the present invention wherein A and $A^1$ are different optionally substituted phenyl groups; and (ii) ring closure of the product resulting from step (i) to give an unsymmetrical TPD compound, preferably using strongly acid condensing agents, for example oleum with a persulphate. This ring closure may introduce sulphonic acid groups into the resultant unsymmetrical TPD compound.

The ring closure step of the fourth aspect of the present invention is described more fully in UK 509898, lines 37 onwards, the incorporation of which is disclosed herein by reference thereto.

According to the seventh aspect of the present invention there is provided an alternative process for the preparation of unsymmetrical TDP compounds wherein a compound of Formula (6) is prepared according to the fifth aspect of the present invention, and is cyclised to an unsymmetrical TPD compound utilising step (ii) of the sixth aspect of the present invention.

Although compounds of the presentation are drawn in the free acid or neutral from it will be appreciated that the present invention includes salts of such compounds.

The invention is further illustrated but not limited by the following Examples in which all parts and percentages are by weight unless otherwise indicated.

EXAMPLE 1

Preparation of 2,3,5-trichloro-6-isopropoxy-1,4-benzoquinone

Chloranil (0.06 mole) and sodium hydrogen carbonate (0.075 mole) were added to 300 ml of methylethylketone (MEK). the mixture was heated to 55° C. before adding iso-propanol (0.5 mole) dropwise with stirring. When the reaction was complete (as judged by HPLC) the MEK solvent was removed from the product mixture under vacuum. The resultant orange gum was recrystallised from petroleum ether to give 2,3,5-trichloro-6-isopropoxy-1,4-benzoquinone as product.

EXAMPLE 2

Preparation of the compound of Formula (7) in which R is prop-2-yl

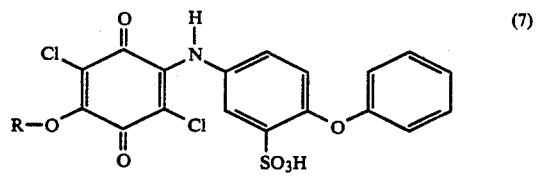

5.0 g of 2,3,5-trichloro-6-isopropoxy-1,4-benzoquinone prepared according to Example 1 was stirred in 250 ml of iso-propanol and the pH adjusted to 7 with sodium hydroxide solution. 2-phenoxy-5-amino benzenesulphonic acid (4.9 g) was added to 100 ml of a 2:3 mixture of isopropanol and acetone and the pH was adjusted to 7 using aqueous sodium hydroxide. The amine solution was then added by means of a dropping funnel to the benzoquinone over several hours at room temperature whilst maintaining at pH 7. The reaction mixture was then filtered and the filter cake was washed with isopropanol before drying under vacuum to provide 1.4 g of symmetrical dianilide by-product which was disposed of. The remaining filtrate was then pooled with the washings and concentrated. The resulting dark solid was added to 200 ml of petroleum ether and heated before filtering whilst still hot. After drying the filter cake 8.0 g of the title monoanilide were recovered. The relative yields of monoanilide:dianilide on a mol/mol basis was 7.8:1.

When analysed by mass spectroscopy using negative ion fast atom bombardment the title product was found to have the expected M/Z of 497.

EXAMPLE 3

Preparation of 2,3,5-trichloro-6-cyclohexanyloxy-1,4-benzoquinone

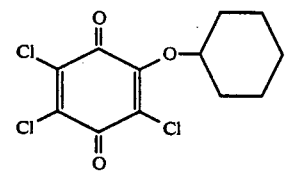

Chloranil (0.06 mole) and sodium hydrogen carbonate (0.075 mole) were added to 300 ml of methyl ethyl ketone (MEK). The mixture was heated to 55° C. before adding cyclohexanol (0.5 mole) dropwise with stirring. When the reaction was complete (as judged by HPLC) the MEK solvent was removed from the product mixture under vacuum. The resultant orange gum was recrystallised from petroleum ether to provide the bright orange crystalline title product (0.04 moles).

The spectral data for the title product is as follows:
$^1H$ NMR (250 MHz, $CDCl_3$, delta) 4.75 (m,1H,CH—O—); 2.0–1.3 (m,10H,5x $CH_2$ cyclohexyl).
$^{13}C$ NMR (BB, $CDCl_3CRACAC$, delta) 173.0, 171.8 (2x C=O); 154.2 (C=C—O); 140.5, 138.8, 127.4 (C=C—Cl); 83.9 (CH—O); 32.7 (2x $CH_2CH$—O); 25.1 ($CH_2CH_2CH$—O); 23.3 ($CH_2CH_2CH_2CH$—O).

Mass Spectrum: m/z: 308 (molecular ion with isotopic evidence of 3 chlorine atoms).

EXAMPLE 4

Preparation of the compound of Formula (7) in which R is cyclohexyl 2.0 g of 2,3,5-trichloro-6-cyclohexyloxy-1,4-benzoquinone prepared as in Example 3 was stirred in 100 ml of acetone and the pH adjusted to 5.6 with sodium hydroxide solution. 2-phenoxy-5-amino benzenesulphonic acid (1.7 g) was dissolved in 30 ml of water and acetone (1:2 mixture) and the pH was adjusted to 7. The amine solution was then added dropwise to the 2,3,5-trichloro-6-cyclohexyloxy-1,4-benzoquinone solution over a period of 30 minutes at room temperature whilst maintaining the pH between 5 and 6. After completion of the reaction the product mixture was shown by HPLC to be composed of 85% monoanilide with a minor amount of symmetrical bis adduct which was removed by filtration.

The spectral data for the title product is as follows:
$^1$H NMR (250 MHz, D$_6$ DMSO, delta) 9.4 (s,1H,NH); 7.5-6.8 (m,8H, 8x CH aromatic); 4.7 (m,1H,CH—O); 2.0-1.3 (m,10H,5x CH$_2$ cyclohexyl).

EXAMPLE 5

Preparation of 2,3,5-trichloro-6-(but-2-oxy)-benzo-1,4-quinone

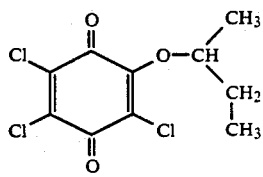

Chloranil (12.3 parts) was dissolved in MEK (300 parts) before adding sodium hydrogen carbonate (8 parts). Aqueous butan-2-ol (50 parts, 1:1) was then added and the mixture was stirred at room temperature until no starting material remained. At the end of the reaction the filtered solution was shown by HPLC to contain 86% title product. The product was used in subsequent reactions without isolation.

When analysed by mass spectroscopy using probe electron impact the title product was found to have the expected M/Z of 282. The $^1$H NMR of the title product in D$_6$DMSO (delta) showed signals at 4.7 (m, 1H, CHO), 1.5-1.7 (m, 2H, CH$_2$), 1.3 (d, 3H, CH$_3$CHOH) and 0.9 (t, 3H, CH$_2$CH$_3$).

EXAMPLE 6

Preparation of 2,3,5-tribromo-6-isopropoxy-1,4-benzoquinone

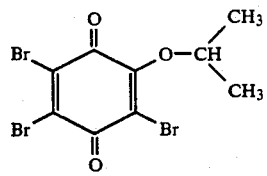

Tetrabromobenzo-1,4-quinone (14.6 parts) was stirred in MEK prior to adding sodium hydrogen carbonate (5.5 parts) and stirring at room temperature. Aqueous propanol (50 parts, 1:1) was added and the reaction was monitored by HPLC until no starting material remained. The resulting solution (which contained 91% 2,3,5-tribromo-6-isopropoxy benzoquinone as judged by HPLC) was recrystallised from 60-80 petrol ether (136 ml) to yield a homogeneous crystalline product (6 parts). The $^1$H NMR of the title product in d$_6$DMSO (delta) showed signals at 5.1 (m, 1H, CH(CH$_3$)$_2$); and 1.4 (d, 6H, CH(CH$_3$)$_2$).

EXAMPLE 7

Preparation of

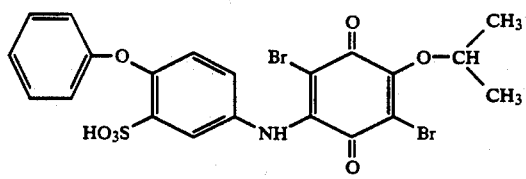

The product from Example 6 (5 parts) was dissolved in isopropanol (250 parts) at pH 7. 3-amino-6-phenoxybenzenesulphonic acid (3.3 parts) was dissolved in a mixture of isopropanol/acetone (57:40 parts) and the resulting solution was added to the pH 7 solution before stirring at room temperature overnight and filtering. The filtrates were concentrated prior to extracting with hot 60-80 petroleum ether and filtering. The product (6.4 parts) was recovered as a dark solid.

When analysed by mass spectroscopy using negative ion fast atom bombardment the title product was found to have the expected M/Z of 497. The $^1$H NMR of the title product in d$_6$DMSO (delta) showed signals at 9.5 (S, 1H(NH)); 7.5-6.7 (m, 8H, Aromatic CH); 5.1 (m, 1H, CH(CH$_3$)$_2$); and 1.4 (d, 6H, CH(CH$_3$)$_2$).

I claim:

1. A compound of the Formula (5):

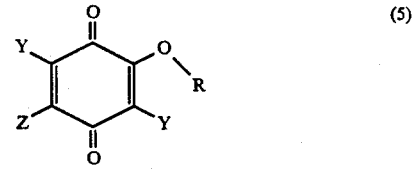

(5)

wherein:
Y is H, alkyl, substituted alkyl, alkoxy, Cl or Br;
R is a group of formula (3)

(3)

R$^1$ and R$^2$ are each independently alkyl, or R$^1$ and R$^2$ together with the carbon atom to which they are attached form an optionally substituted 4, 5 or 6 membered alicyclic or heterocyclic ring;
R$^3$ is H;
Z is Cl, Br or A—NH—; and
A is H, optionally substituted alkyl, optionally substituted aralkyl or optionally substituted aryl.

2. A compound according to claim 1 wherein Z is Cl or Br.

3. A compound according to claim 1 wherein Z is A—NH— wherein A is as defined in claim 1.

4. A compound according to claim 1 or claim 3 wherein A is optionally substituted phenyl.

5. A compound according to claim 1 wherein Y and Z are both Cl and R$^1$ and R$^2$ are both methyl.

6. A compound according to claim 1 wherein Y and Z are independently Cl or Br and R$^1$ and R$^2$ are both alkyl.

* * * * *